United States Patent
Smith

(10) Patent No.: US 7,998,745 B2
(45) Date of Patent: Aug. 16, 2011

(54) IMPEDANCE SYSTEMS, DEVICES, AND METHODS FOR EVALUATING IONTOPHORETIC PROPERTIES OF COMPOUNDS

(75) Inventor: Gregory A. Smith, Issaquah, WA (US)

(73) Assignee: TTI ellebeau, Inc., Tokyo (JP)

( * ) Notice: Subject to any disclaimer, the term of this patent is extended or adjusted under 35 U.S.C. 154(b) by 547 days.

(21) Appl. No.: 11/850,597

(22) Filed: Sep. 5, 2007

(65) Prior Publication Data

US 2008/0054913 A1   Mar. 6, 2008

Related U.S. Application Data

(60) Provisional application No. 60/842,439, filed on Sep. 5, 2006.

(51) Int. Cl.
*G01R 27/02* (2006.01)
*G01R 27/26* (2006.01)

(52) U.S. Cl. ........ 436/149; 324/686; 324/693; 204/477; 204/550

(58) Field of Classification Search ................ 436/149; 324/686, 693; 204/477, 550
See application file for complete search history.

(56) References Cited

U.S. PATENT DOCUMENTS

| | | | |
|---|---|---|---|
| 4,640,689 A * | 2/1987 | Sibalis | 604/20 |
| 5,291,887 A | 3/1994 | Stanley et al. | 128/637 |
| 5,395,310 A | 3/1995 | Untereker et al. | 604/20 |
| 5,582,586 A | 12/1996 | Tachibana et al. | 604/20 |
| 6,245,057 B1 | 6/2001 | Sieben et al. | 604/891.1 |
| 6,391,015 B1 | 5/2002 | Millot | 604/503 |
| 6,437,551 B1 * | 8/2002 | Krulevitch et al. | 324/71.1 |
| 6,692,456 B1 | 2/2004 | Eppstein et al. | 604/22 |
| 6,928,318 B2 | 8/2005 | Simon | 604/20 |
| 6,939,311 B2 | 9/2005 | Geiger | 600/573 |
| 7,018,345 B2 | 3/2006 | Mori et al. | 600/573 |
| 2002/0182485 A1 | 12/2002 | Anderson et al. | 429/105 |
| 2003/0088205 A1 | 5/2003 | Chandrasekaran et al. | 604/20 |
| 2003/0185023 A1 | 10/2003 | Hause, Jr. | 363/31 |
| 2004/0087671 A1 | 5/2004 | Tamada et al. | 516/99 |
| 2004/0248320 A1 | 12/2004 | Santini, Jr. et al. | 436/174 |
| 2005/0267440 A1 | 12/2005 | Herman et al. | 604/501 |
| 2006/0024358 A1 | 2/2006 | Santini et al. | 424/448 |
| 2006/0094946 A1 | 5/2006 | Kellogg et al. | 600/347 |
| 2006/0095001 A1 | 5/2006 | Matsumura et al. | 604/20 |
| 2006/0116628 A1 | 6/2006 | Matsumura et al. | 604/20 |

(Continued)

FOREIGN PATENT DOCUMENTS

EP   0904801 A2   3/1999

(Continued)

OTHER PUBLICATIONS

The Enhanced Iontophoretic Transport of TRH and its Impedance Study Wei-Lung Chou, Ching-Hsiung Cheng, Shi-Chern Yen, Tsung-Shann Jiang Drug Development and Industrial Pharmacy 22(9&10), 943-950, 1996.*

(Continued)

*Primary Examiner* — Robert J Hill, Jr.
*Assistant Examiner* — Dwan A Gerido
(74) *Attorney, Agent, or Firm* — Seed IP Law Group PLLC

(57) ABSTRACT

Systems, devices, and methods for evaluating iontophoretic properties of compounds. An impedance spectrometer is operable to determine an impedance of a compound and a processor is configured to compare the determined impedance of the compound to a database of stored values.

15 Claims, 3 Drawing Sheets

U.S. PATENT DOCUMENTS

| | | |
|---|---|---|
| 2006/0129085 A1 | 6/2006 | Tanioka et al. .................. 604/20 |
| 2006/0135906 A1 | 6/2006 | Matsumura et al. ............ 604/20 |
| 2006/0173401 A1 | 8/2006 | Tanioka et al. .................. 604/20 |
| 2006/0286102 A1 | 12/2006 | Jin et al. ...................... 424/143.1 |
| 2008/0058756 A1 | 3/2008 | Smith ........................... 604/501 |
| 2008/0208106 A1 | 8/2008 | Kogure et al. ................... 604/20 |

FOREIGN PATENT DOCUMENTS

| | | |
|---|---|---|
| EP | 0 931 564 A1 | 7/1999 |
| EP | 1 440 707 A1 | 7/2004 |
| JP | 06-070987 | 3/1994 |
| JP | 3-40517 | 3/2000 |
| JP | 2000-229128 | 8/2000 |
| JP | 2000-229129 | 8/2000 |
| JP | 2000-237326 | 9/2000 |
| JP | 2000-237327 | 9/2000 |
| JP | 2000-237328 | 9/2000 |
| JP | 2000-237329 | 9/2000 |
| JP | 2000-288097 | 10/2000 |
| JP | 2000-288098 | 10/2000 |
| JP | 2001-120670 | 5/2001 |
| JP | 2001-523996 | 11/2001 |
| JP | 2004-024699 | 1/2004 |
| JP | 2004-317317 | 10/2004 |
| JP | 2004-357313 | 12/2004 |
| JP | 2006-149891 | 6/2006 |
| JP | 2006-212194 | 8/2006 |
| JP | 2006-262943 | 10/2006 |
| WO | WO 03/037425 | 5/2003 |
| WO | 2006/055729 | 5/2006 |
| WO | 2007/010900 | 1/2007 |
| WO | 2007041115 A1 | 4/2007 |
| WO | 2008027218 A2 | 3/2008 |

OTHER PUBLICATIONS

U.S. Appl. No. 11/850,602, filed Sep. 5, 2007, Smith.

U.S. Appl. No. 60/627,952, filed Nov. 16, 2004, Matsumura et al.

U.S. Appl. No. 60/842,439, filed Sep. 5, 2006, Smith.

Asher et al., "Photonic Crystal Carbohydrate Sensors: Low Ionic Strength Sugar Sensing" *Journal of the American Chemical Society* 125(11):3322-3329, 2003.

JCAAI.org, "Diagnostic Tests of Cell Mediated Immune Reactions (Delayed Hypersensitivity)," *Annals of Allergy* 75:543-625, 1995. URL-http://www.jcaai.org//pp/adt_3-02.asp, retrieved Aug. 23, 2007, 2 pages.

Merclin et al. "Iontophoretic delivery of 5-aminolevulinic acid and its methyl ester using a carbopol gel as vehicle," *Journal of Controlled Release* 98 (1):57-65, 2004.

Hirvonen, J., et al., "Experimental Verification of the Mechanistic Model for Transdermal Transport Including Iontophoresis," *J. Controlled Release*, 56:169-174, 1998.

Krämer, S., "Absorption Prediction from Physicochemical Parameters," *Pharm Sci Technolo Today*, 2(9):373-380, Sep. 1999.

\* cited by examiner

US 7,998,745 B2

IMPEDANCE SYSTEMS, DEVICES, AND METHODS FOR EVALUATING IONTOPHORETIC PROPERTIES OF COMPOUNDS

CROSS-REFERENCE TO RELATED APPLICATION

This application claims the benefit under 35 U.S.C. §119(e) of U.S. Provisional Patent Application No. 60/842,439 filed Sep. 5, 2006, the content of which is incorporated herein by reference in its entirety.

BACKGROUND

1. Field

The present disclosure generally relates to the field of iontophoresis and, more particularly, to systems, devices, and methods for evaluating iontophoretic properties of compounds.

2. Description of the Related Art

Iontophoresis employs an electromotive force and/or current to transfer an active agent (e.g., a charged substance, an ionized compound, an ionic drug, a therapeutic, a bioactive-agent, and the like), to a biological interface (e.g., skin, mucus membrane, and the like), by using a small electrical charge applied to an iontophoretic chamber containing a similarly charged active agent and/or its vehicle.

Iontophoresis devices typically include an active electrode assembly and a counter electrode assembly, each coupled to opposite poles or terminals of a power source, for example a chemical battery. Each electrode assembly typically includes a respective electrode element to apply an electromotive force and/or current. Such electrode elements often comprise a sacrificial element or compound, for example silver or silver chloride.

The active agent may be either cationic or anionic, and the power source may be configured to apply the appropriate voltage polarity based on the polarity of the active agent. Iontophoresis may be advantageously used to enhance or control the delivery rate of the active agent. The active agent may be stored in a reservoir such as a cavity. See e.g., U.S. Pat. No. 5,395,310. Alternatively, the active agent may be stored in a reservoir such as a porous structure or a gel. An ion exchange membrane may be positioned to serve as a polarity selective barrier between the active agent reservoir and the biological interface. The membrane, typically only permeable with respect to one particular type of ion (e.g., a charged active agent), prevents the back flux of oppositely charged ions from the skin or mucous membrane.

Commercial acceptance of iontophoresis devices is dependent on a variety of factors, such as cost to manufacture, shelf life or stability during storage, efficiency, and/or timeliness of active agent delivery, biological capability, and/or disposal issues. Commercial acceptance of iontophoresis devices is also dependent on the availability of iontophoretic deliverable drugs. Therefore, it may be desirable to have novel approaches for screening libraries of drugs that could potentially be delivered using iontophoresis.

The present disclosure is directed to overcoming one or more of the shortcomings set forth above, and providing further related advantages.

BRIEF SUMMARY

In one aspect, the present disclosure is directed to a system for evaluating a compound candidate for iontophoretic drug delivery. The system includes an impedance spectrometer and a processor. The impedance spectrometer may be operable to determine an impedance of a compound and the processor may be configured to compare the determined impedance of the compound to a database of stored values. The system may further include an iontophoretic drug delivery device operable to deliver the compound.

In another aspect, the present disclosure is directed to a method for screening candidate drugs for iontophoretic delivery. The method includes applying an alternating current to a bulk solution comprising at least one drug candidate, measuring the impedance response of the bulk solution comprising the at least one drug candidate, and ranking the at least one drug candidate based in part on the determined impedance response of the bulk solution comprising the at least one drug candidate.

In another aspect, the present disclosure is directed to an assay for determining the iontophoretic deliverability of a pharmaceutical composition. The assay includes evaluating at least one resistive or capacitive property of the pharmaceutical composition, and correlating the at least one resistive or capacitive property to an iontophoretic transport value estimate for the pharmaceutical composition. The assay may further include ranking the compound based in part on the iontophoretic transport value estimate.

In yet another aspect, the present disclosure is directed to a method for evaluating drug candidates for iontophoretic drug therapy. The method includes evaluating the ionic mobility of a composition comprising at least one drug candidate in a bulk solution, evaluating the ionic mobility of a composition comprising at least one drug candidate through one or more resistive elements, correlating the ionic mobility in a bulk solution to the ionic mobility through one or more resistive elements, and determining an iontophoretic transport value estimate for the drug candidate.

BRIEF DESCRIPTION OF THE SEVERAL VIEWS OF THE DRAWINGS

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements, as drawn, are not intended to convey any information regarding the actual shape of the particular elements, and have been solely selected for ease of recognition in the drawings.

DETAILED DESCRIPTION

Figure 1:
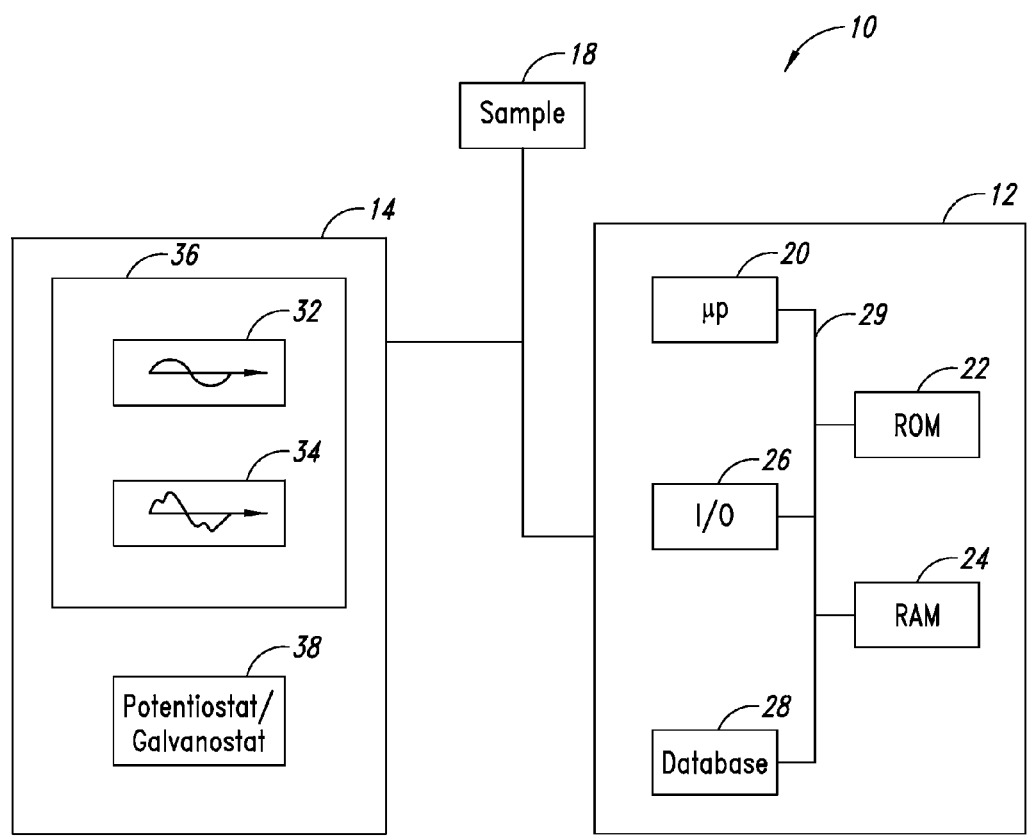
FIG. 1 is a functional block diagram showing a system for evaluating a compound candidate for iontophoretic drug delivery according to one illustrative embodiment.

In the following description, certain specific details are included to provide a thorough understanding of various disclosed embodiments. One skilled in the relevant art, however, will recognize that embodiments may be practiced without one or more of these specific details, or with other methods, components, materials, etc. In other instances, well-known structures associated with impedance spectrometers, such as electrolytic sample cells, waveform generators, digital correlators, frequency response analyzers, and the like have not been shown or described in detail to avoid unnecessarily obscuring descriptions of the embodiments.

Unless the context requires otherwise, throughout the specification and claims which follow, the word "comprise" and variations thereof, such as, "comprises" and "comprising" are to be construed in an open, inclusive sense, that is as "including, but not limited to."

Reference throughout this specification to "one embodiment," or "an embodiment," or "another embodiment" means that a particular referent feature, structure, or characteristic described in connection with the embodiment is included in at least one embodiment. Thus, the appearances of the phrases "in one embodiment," or "in an embodiment," or "another embodiment" in various places throughout this specification are not necessarily all referring to the same embodiment. Furthermore, the particular features, structures, or characteristics may be combined in any suitable manner in one or more embodiments.

It should be noted that, as used in this specification and the appended claims, the singular forms "a," "an," and "the" include plural referents unless the content clearly dictates otherwise. Thus, for example, reference to a system for evaluating a compound candidate for iontophoretic drug delivery including "a processor" includes a single processor, or two or more processors. It should also be noted that the term "or" is generally employed in its sense including "and/or" unless the content clearly dictates otherwise.

As used herein the term "membrane" means a boundary, a layer, barrier, or material, which may, or may not be permeable. The term "membrane" may further refer to an interface. Unless specified otherwise, membranes may take the form a solid, liquid, or gel, and may or may not have a distinct lattice, non cross-linked structure, or cross-linked structure.

As used herein the term "ion selective membrane" means a membrane that is substantially selective to ions, passing certain ions while blocking passage of other ions. An ion selective membrane for example, may take the form of a charge selective membrane, or may take the form of a semi-permeable membrane.

As used herein the term "charge selective membrane" means a membrane that substantially passes and/or substantially blocks ions based primarily on the polarity or charge carried by the ion. Charge selective membranes are typically referred to as ion exchange membranes, and these terms are used interchangeably herein and in the claims. Charge selective or ion exchange membranes may take the form of a cation exchange membrane, an anion exchange membrane, and/or a bipolar membrane. A cation exchange membrane substantially permits the passage of cations and substantially blocks anions. Examples of commercially available cation exchange membranes include those available under the designators NEOSEPTA, CM-1, CM-2, CMX, CMS, and CMB from Tokuyama Co., Ltd. Conversely, an anion exchange membrane substantially permits the passage of anions and substantially blocks cations. Examples of commercially available anion exchange membranes include those available under the designators NEOSEPTA, AM-1, AM-3, AMX, AHA, ACH, and ACS, also from Tokuyama Co., Ltd.

As used herein and in the claims, the term "bipolar membrane" means a membrane that is selective to two different charges or polarities. Unless specified otherwise, a bipolar membrane may take the form of a unitary membrane structure, a multiple membrane structure, or a laminate. The unitary membrane structure may include a first portion including cation ion exchange materials or groups and a second portion opposed to the first portion, including anion ion exchange materials or groups. The multiple membrane structure (e.g., two-film structure) may include a cation exchange membrane laminated or otherwise coupled to an anion exchange membrane. The cation and anion exchange membranes initially start as distinct structures, and may or may not retain their distinctiveness in the structure of the resulting bipolar membrane.

As used herein and in the claims, the term "semi-permeable membrane" means a membrane that is substantially selective based on a size or molecular weight of the ion. Thus, a semi-permeable membrane substantially passes ions of a first molecular weight or size, while substantially blocking passage of ions of a second molecular weight or size, greater than the first molecular weight or size. In some embodiments, a semi-permeable membrane may permit the passage of some molecules at a first rate, and some other molecules at a second rate different from the first. In yet further embodiments, the "semi-permeable membrane" may take the form of a selectively permeable membrane allowing only certain selective molecules to pass through it.

As used herein and in the claims, the term "porous membrane" means a membrane that is not substantially selective with respect to ions at issue. For example, a porous membrane is one that is not substantially selective based on polarity, and not substantially selective based on the molecular weight or size of a subject element or compound.

As used herein and in the claims, the term "gel matrix" means a type of reservoir, which takes the form of a three-dimensional network, a colloidal suspension of a liquid in a solid, a semi-solid, a cross-linked gel, a non cross-linked gel, a jelly-like state, and the like. In some embodiments, the gel matrix may result from a three-dimensional network of entangled macromolecules (e.g., cylindrical micelles). In some embodiments, a gel matrix may include hydrogels, organogels, and the like. Hydrogels refer to three-dimensional network of, for example, cross-linked hydrophilic polymers in the form of a gel and substantially composed of water. Hydrogels may have a net positive or negative charge, or may be neutral.

As used herein and in the claims, the term "reservoir" means any form of mechanism to retain an element, compound, pharmaceutical composition, active agent, and the like, in a liquid state, solid state, gaseous state, mixed state and/or transitional state. For example, unless specified otherwise, a reservoir may include one or more cavities formed by a structure, and may include one or more ion exchange membranes, semi-permeable membranes, porous membranes and/or gels if such are capable of at least temporarily retaining an element or compound. Typically, a reservoir serves to retain a biologically active agent prior to the discharge of such agent by electromotive force and/or current into the biological interface. A reservoir may also retain an electrolyte solution.

As used herein and in the claims, the term "active agent" refers to a compound, molecule, or treatment that elicits a biological response from any host, animal, vertebrate, or invertebrate, including for example fish, mammals, amphibians, reptiles, birds, and humans. Examples of active agents include therapeutic agents, pharmaceutical agents, pharmaceuticals (e.g., a drug, a therapeutic compound, pharmaceutical salts, and the like) non-pharmaceuticals (e.g., a cosmetic substance, and the like), a vaccine, an immunological agent, a local or general anesthetic or painkiller, an antigen or a protein or peptide such as insulin, a chemotherapy agent, an anti-tumor agent.

In some embodiments, the term "active agent" refers to the active agent, as well as its pharmacologically active salts, pharmaceutically acceptable salts, prodrugs, metabolites, analogs, and the like. In some further embodiment, the active agent includes at least one ionic, cationic, ionizeable, and/or neutral therapeutic drug and/or pharmaceutical acceptable salts thereof. In yet other embodiments, the active agent may include one or more "cationic active agents" that are positively charged, and/or are capable of forming positive charges in aqueous media. For example, many biologically active agents have functional groups that are readily convertible to a positive ion or can dissociate into a positively charged ion and a counter ion in an aqueous medium. Other active agents may be polarized or polarizable, that is exhibiting a polarity at one portion relative to another portion. For instance, an active agent having an amino group can typically take the form an ammonium salt in solid state and dissociates into a free ammonium ion ($NH_4^+$) in an aqueous medium of appropriate pH. The term "active agent" may also refer to neutral agents, molecules, or compounds capable of being delivered via electro-osmotic flow. The neutral agents are typically carried by the flow of, for example, a solvent during electrophoresis. Selection of the suitable active agents is therefore within the knowledge of one skilled in the relevant art.

In some embodiments, one or more active agents may be selected from analgesics, anesthetics, anesthetics vaccines, antibiotics, adjuvants, immunological adjuvants, immunogens, tolerogens, allergens, toll-like receptor agonists, toll-like receptor antagonists, immuno-adjuvants, immuno-modulators, immuno-response agents, immuno-stimulators, specific immuno-stimulators, non-specific immuno-stimulators, and immuno-suppressants, or combinations thereof.

Non-limiting examples of such active agents include lidocaine, articaine, and others of the -caine class; morphine, hydromorphone, fentanyl, oxycodone, hydrocodone, buprenorphine, methadone, and similar opiod agonists; sumatriptan succinate, zolmitriptan, naratriptan HCl, rizatriptan benzoate, almotriptan malate, frovatriptan succinate and other 5-hydroxytryptamine 1 receptor subtype agonists; resiquimod, imiquidmod, and similar TLR 7 and 8 agonists and antagonists; domperidone, granisetron hydrochloride, ondansetron and such anti-emetic drugs; zolpidem tartrate and similar sleep inducing agents; L-dopa and other anti-Parkinson's medications; aripiprazole, olanzapine, quetiapine, risperidone, clozapine, and ziprasidone, as well as other neuroleptica; diabetes drugs such as exenatide; as well as peptides and proteins for treatment of obesity and other maladies.

Further non-limiting examples of active agents include ambucaine, amethocaine, isobutyl p-aminobenzoate, amolanone, amoxecaine, amylocaine, aptocaine, azacaine, bencaine, benoxinate, benzocaine, N,N-dimethylalanylbenzocaine, N,N-dimethylglycylbenzocaine, glycylbenzocaine, beta-adrenoceptor antagonists betoxycaine, bumecaine, bupivicaine, levobupivicaine, butacaine, butamben, butanilicaine, butethamine, butoxycaine, metabutoxycaine, carbizocaine, carticaine, centbucridine, cepacaine, cetacaine, chloroprocaine, cocaethylene, cocaine, pseudococaine, cyclomethycaine, dibucaine, dimethisoquin, dimethocaine, diperodon, dyclonine, ecognine, ecogonidine, ethyl aminobenzoate, etidocaine, euprocin, fenalcomine, fomocaine, heptacaine, hexacaine, hexocaine, hexylcaine, ketocaine, leucinocaine, levoxadrol, lignocaine, lotucaine, marcaine, mepivacaine, metacaine, methyl chloride, myrtecaine, naepaine, octacaine, orthocaine, oxethazaine, parenthoxycaine, pentacaine, phenacine, phenol, piperocaine, piridocaine, polidocanol, polycaine, prilocaine, pramoxine, procaine (Novocaine®), hydroxyprocaine, propanocaine, proparacaine, propipocaine, propoxycaine, pyrrocaine, quatacaine, rhinocaine, risocaine, rodocaine, ropivacaine, salicyl alcohol, tetracaine, hydroxytetracaine, tolycaine, trapencaine, tricaine, trimecaine tropacocaine, zolamine, a pharmaceutically acceptable salt thereof, and mixtures thereof.

As used herein and in the claims, the term "subject" generally refers to any host, animal, vertebrate, or invertebrate, and includes fish, mammals, amphibians, reptiles, birds, and particularly humans.

The headings provided herein are for convenience only and do not interpret the scope or meaning of the embodiments.

FIG. 1 shows an exemplary system 10 for evaluating a compound candidate for iontophoretic drug delivery. The system 10 includes a control system 12 and an impedance spectrometer 14. The system 10 may further include an electrolytic sample cell 18.

Impedance is a measure of opposition to electrical current flow, and typically refers to the relationship between the voltage across a sample element and the current through the sample element. The electrical current flow results, in part, from an ionic movement response to the applied potential difference. If the applied potential (excitation or input signal) is sinusoidal (e.g., $E=E_0 \sin[\omega t]$), then the subsequent current (response or output signal) will also be sinusoidal, with a value of $I=I_0 \sin[\omega t+\phi]$. The relationship between the applied potential (E) and the current flow (I) is known as the impedance (Z). Impedance (Z) has a magnitude (amplitude) of (|Z|) and phase ($\phi$) and is generally expressed as a complex vector sum of resistance (R) and reactance (X). Frequency response refers to the transfer characteristic of a system, that is, the input/output relationship. For example, the magnitude and phase shift of an alternating current (AC) response of a sample element to an applied AC.

The impedance spectrometer 14 is operable to determine an impedance of a compound candidate and may include an input signal generator 32 (e.g., a sine wave generator) configured to provide an input signal of programmable amplitude and frequency, and one or more response analyzers 34 configured to obtain magnitude and phase information from a signal response. The input signal generator 32 and one or more response analyzers 34 can be included in a single frequency response analyzer (FRA) 36, or provided as separate components. The impedance spectrometer 14 may further include a potentiostat/galvanostat 38.

In some embodiments, the FRA 36 is configured to apply an excitation signal to an electrode assembly, an electrolytic cell, an iontophoretic delivery patch, and/or iontophoresis device that includes a compound candidate for iontophoretic drug delivery. The FRA 36 may further be configured to analyze a response signal resulting from the excitation signal. In an embodiment, the FRA 36 may be configured to provide impedance measurements in a stand-alone mode, suitable for making two or four electrode impedance measurements.

The impedance spectrometer 14 may further be operable to determine the impedance of the compound candidate for at least two selected frequencies of an alternating current. In another embodiment, the impedance spectrometer 14 may be operable to determine the impedance of the compound candidate by applying a frequency-swept sine wave to the compound candidate, and examining the response signals using the one or more response analyzers 34. Determining the impedance may include, for example, determining at least one of an amplitude and phase shift of a measured signal of the compound candidate for at least two selected frequencies of an alternating current. In an embodiment, the frequency of the alternating current is selected from a range of about 10 µHz to about 1 MHz. In another embodiment, the frequency of the alternating current is selected from three or more regions of a frequency spectrum.

The control system 12 may include one or more controllers such as a microprocessor 20, a digital signal processor (DSP) (not shown), an application-specific integrated circuit (ASIC) (not shown), and the like. The control system 12 may also include one or more memories, for example, read-only memory (ROM) 22 random access memory (RAM) 24, and the like, coupled to the controllers 20 by one or more busses 29. The control system 12 may further include one or more input devices 26 (e.g., a display, a mouse, a keyboard, and other peripheral devices). In an embodiment, the microprocessor 20 may be configured to compare the determined impedance of the compound candidate to a database 28 of stored values. The database 28 of stored values may include impedance data, flux data, ionic conductivity data, resistance data, reactance data, ionic mobility data, diffusion coefficients, transport numbers, statistical averages data for general iontophoretic trends, and the like. The database 28 of stored values may further include partition coefficient ClogD data, molecular weight data, ionic charge data, lipophilicity data, solubility data, charge to mass ration data, ionic mobility data, reaction kinetic data, reduction-oxidation potential data, and the like. In an embodiment, the microprocessor 20 may further be configured to rank the compound candidate based in part on a determined flux value based in part on the measured impedance.

Figure 2:
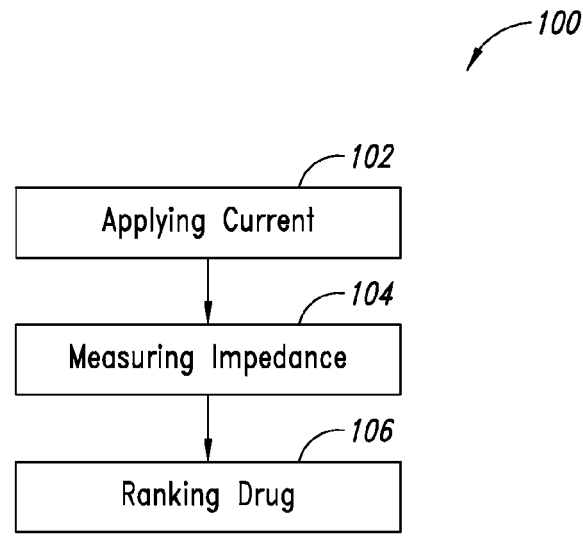
FIG. 2 is a flow diagram of a method for screening candidate drugs for iontophoretic delivery according to another illustrative embodiment.

FIG. 2 shows a method 100 for screening candidate drugs for iontophoretic delivery according to another illustrative embodiment.

At 102, the method 100 includes applying an alternating current to a bulk solution comprising at least one drug candidate. For example, the FPA 36 is configured to apply an alternating current to a bulk solution comprising the at least one drug candidate. The applied alternating current may include an input signal of programmable amplitude and frequency, a frequency-swept sine wave, a generated waveform, a single sine wave, a multi-sine wave, and the like. In certain embodiments, the alternating current is applied to a bulk solution comprising the at least one drug candidate included in an iontophoretic delivery patch, an iontophoretic drug delivery device, an electrolytic sample cell, and the like.

At 104, the method includes measuring the impedance response of the bulk solution comprising the at least one drug candidate. For example, the one or more response analyzers 34 may be configured to analyze the impedance response of a bulk solution comprising the at least one drug candidate to the applied alternating current. In some embodiments, measuring the impedance response may include employing one or more data acquisition techniques including alternating current bridges (e.g., for measuring ac resistance, capacitance, and inductance), fast fourier transform techniques, lissajous figures, and phase sensitive detectors (e.g., lock-in amplifiers), sine correlation, and the like. Measuring the impedance response may further include measuring the impedance response at two or more frequencies of the alternating current, and obtaining at least one of an amplitude or a phase shift for each response signal. In certain embodiments, measuring the impedance response may further include measuring the impedance response of a composition comprising at least one drug candidate through at least one resistive element. Examples of a resistive element include an iontophoretic delivery patch, an iontophoresis device, a membrane (e.g., an ion selective membrane, a charge selective membrane, a bipolar membrane, a semi-permeable membrane, a porous membrane, gel-matrix, and the like), a reservoir, an electrolytic cell, and the like. In an embodiment, the resistive element includes an iontophoretic drug delivery device operable to deliver the at least one drug candidate.

At 106, after determining an impedance response, the at least one drug candidate is ranked, based in part, on the corresponding measured impedance response 104. Ranking may include comparing the measured impedance response to a database 28 of stored values. As previously noted, the stored values may include impedance data, flux data, ionic conductivity data, resistance data, reactance data, ionic mobility data, diffusion coefficients, and the like. The processor 20 may further be configured to rank the at least one drug candidate based in part on a determined flux value based in part on the measured impedance. In an embodiment, ranking may further include correlating the corresponding measured impedance response to a property including a partition coefficient ClogD, a molecular weight, an ionic charge, a lipophilicity, a solubility, a charge to mass ration, an ionic mobility, and the like, and ranking the drug candidate based in part on the correlated property.

Figure 3:
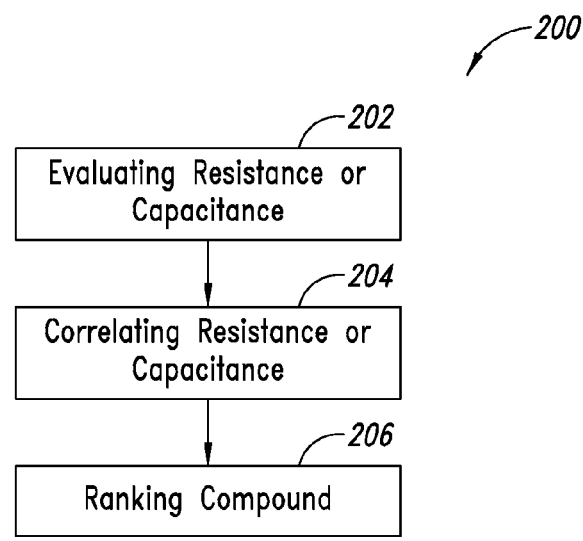
FIG. 3 is a flow diagram of an assay for determining the iontophoretic deliverability of a pharmaceutical composition according to another illustrative embodiment.

FIG. 3 shows an assay 200 for determining the iontophoretic deliverability of a pharmaceutical composition according to another illustrative embodiment. The pharmaceutical composition may include, for example, at least one candidate drug compound, therapeutic agent, active agent, or pharmaceutical salts thereof.

At 202, at least one resistive or capacitive property of the pharmaceutical composition is evaluated. Examples of a resistive or capacitive property include impedance, ionic mobility, a diffusion coefficient, a flux, a transport number, and the like.

Evaluating the at least one resistive or capacitive property of the pharmaceutical composition may include applying an alternating current to a bulk solution comprising the pharmaceutical composition, and measuring an impedance response of the pharmaceutical composition with the impedance spectrometer 14. In an embodiment, evaluating the at least one resistive or capacitive property of the pharmaceutical composition may include applying an alternating current to a bulk solution comprising the pharmaceutical composition, and obtaining at least one of a magnitude or a phase shift of a response signal for the pharmaceutical composition, with the impedance spectrometer 14, at two or more frequencies of the alternating current. In another embodiment, evaluating the at least one resistive or capacitive property of the pharmaceutical composition may include applying an alternating current to an iontophoretic drug delivery patch including the pharmaceutical composition, and measuring an impedance response of the pharmaceutical composition with an impedance spectrometer 14. In some embodiments, measuring the impedance response of the pharmaceutical composition may include measuring the impedance response at two or more frequencies of the alternating current. In some embodiments, evaluating the at least one resistive or capacitive property of the pharmaceutical composition may further include evaluating the reaction kinetics of the pharmaceutical composition, candidate drug compound, therapeutic agent, active agent, as well as other compounds of interest intended to be used as redox (reduction-oxidation) reagents in an electrode system requiring such. In some other embodiments, evaluating the at least one resistive or capacitive property of the pharmaceutical composition may further include evaluating the adsorption properties (e.g., physicochemical properties, physiological processes affecting drug absorption, effect on reaction kinetics, and the like) of the pharmaceutical composition, candidate drug compound, therapeutic agent, active agent, as well as other compounds of interest.

At 204, the at least one resistive or capacitive property is correlated to an iontophoretic transport value estimate for the pharmaceutical composition. Correlating may include, for example, performing a comparison of the at least one resistive or capacitive property to stored resistive and/or capacitive property data for compounds of like charge and/or chemical properties. In some embodiments, the one or more controllers such as a microprocessor 20 may be configured to correlate the at least one resistive or capacitive property to an iontophoretic transport value estimate for the pharmaceutical composition.

At 206, the pharmaceutical composition is ranked based in part on the determined iontophoretic transport value estimate. Ranking may include performing a comparison of the transport value estimate for the pharmaceutical composition to stored transport data for other pharmaceutical composition. In some embodiments, the one or more controllers such as a microprocessor 20 may be configured to rank the pharmaceutical composition based in part on the determined iontophoretic transport value estimate.

Figure 4:
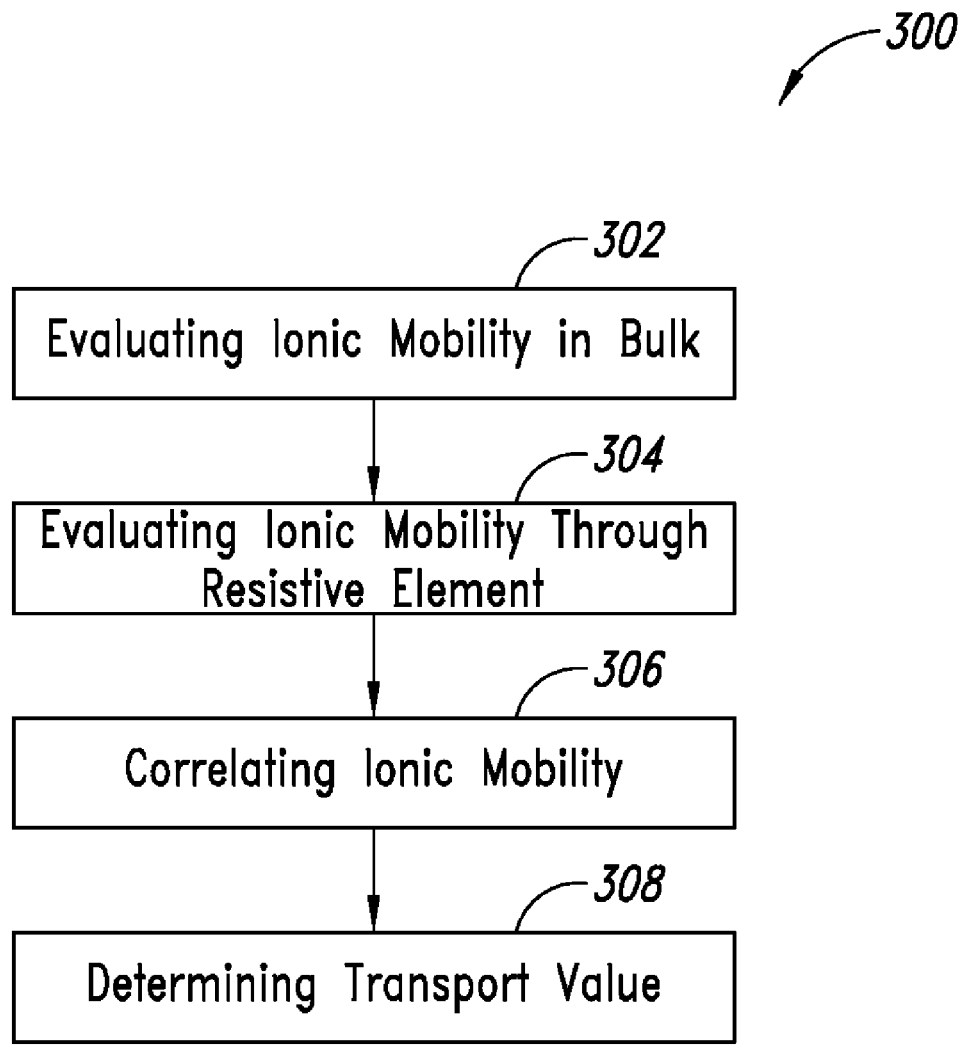
FIG. 4 is a flow diagram of a method for evaluating drug candidates for iontophoretic drug therapy according to another illustrative embodiment.

FIG. 4 shows a method 300 for evaluating drug candidates for iontophoretic drug therapy.

At 302, the ionic mobility of a composition including at least one drug candidate in a bulk solution is evaluated. At 304, the ionic mobility of a composition comprising at least one drug candidate through one or more resistive elements is evaluated.

In an embodiment, evaluating the ionic mobility includes applying an alternating current to a composition comprising at least one drug candidate and measuring an impedance response with an impedance spectrometer 14. The impedance response may include at least one of a measured signal amplitude and a measured signal phase shift. Evaluating the ionic mobility may further include applying an alternating current at two or more frequencies to a composition comprising at least one drug candidate, and measuring an impedance response of a corresponding response signal.

At 306, the ionic mobility evaluated from the composition including at least one drug candidate in a bulk solution is correlated to the ionic mobility evaluated through the one or more resistive elements. Correlating may include correlating the ionic mobility of at least one drug candidate in a bulk solution and the ionic mobility through the at least one or more resistive elements to a stored transport value. Correlating may further include establishing a statistical relationship between the ionic mobility of at least one drug candidate in a bulk solution to the ionic mobility through of the at least one or more resistive elements. In an embodiment, the one or more resistive elements may include an iontophoretic delivery patch.

At 307, an iontophoretic transport value estimate for the drug candidate is determined. Determining the iontophoretic transport value estimate may include dividing a current density associated with the drug candidate by the sum of current densities of all the ions present in, for example, the pharmaceutical composition, and/or the like, and correlating that fraction to the ionic mobility of the composition including at least one drug candidate in a bulk solution and/or to the ionic mobility through one or more resistive elements.

The above description of illustrated embodiments, including what is described in the Abstract, is not intended to be exhaustive or to limit the embodiments to the precise forms disclosed. Although specific embodiments of and examples are described herein for illustrative purposes, various equivalent modifications can be made without departing from the spirit and scope of the disclosure, as will be recognized by those skilled in the relevant art. The teachings provided herein of the various embodiments can be applied to other problem-solving systems devices, and methods, not necessarily the exemplary problem-solving systems devices, and methods generally described above.

For instance, the foregoing detailed description has set forth various embodiments of the systems, devices, and/or methods via the use of block diagrams, schematics, and examples. Insofar as such block diagrams, schematics, and examples contain one or more functions and/or operations, it will be understood by those skilled in the art that each function and/or operation within such block diagrams, flowcharts, or examples can be implemented, individually and/or collectively, by a wide range of hardware, software, firmware, or virtually any combination thereof. In one embodiment, the present subject matter may be implemented via Application Specific Integrated Circuits (ASICs). However, those skilled in the art will recognize that the embodiments disclosed herein, in whole or in part, can be equivalently implemented in standard integrated circuits, as one or more computer programs running on one or more computers (e.g., as one or more programs running on one or more computer systems), as one or more programs running on one or more controllers (e.g., microcontrollers) as one or more programs running on one or more processors (e.g., microprocessors), as firmware, or as virtually any combination thereof, and that designing the circuitry and/or writing the code for the software and or firmware would be well within the skill of one of ordinary skill in the art in light of this disclosure.

In addition, those skilled in the art will appreciate that the mechanisms of taught herein are capable of being distributed as a program product in a variety of forms, and that an illustrative embodiment applies equally regardless of the particular type of signal bearing media used to actually carry out the distribution. Examples of signal bearing media include, but are not limited to, the following: recordable type media such as floppy disks, hard disk drives, CD ROMs, digital tape, and computer memory; and transmission type media such as digital and analog communication links using TDM or IP based communication links (e.g., packet links).

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety, including but not limited to: U.S. Provisional Patent Application No. 60/842,439; filed Sep. 5, 2007, Japanese patent application Serial No. H03-86002, filed Mar. 27, 1991, having Japanese Publication No. H04-297277, issued on Mar. 3, 2000 as Japanese Patent No. 3040517; Japanese patent application Serial No. 11-033076, filed Feb. 10, 1999, having Japanese Publication No. 2000-229128; Japanese patent application Serial No. 11-033765, filed Feb. 12, 1999, having Japanese Publication No. 2000-229129; Japanese patent application Serial No. 11-041415, filed Feb. 19, 1999, having Japanese Publication No. 2000-237326; Japanese patent application Serial No. 11-041416, filed Feb. 19, 1999, having Japanese Publication No. 2000-237327; Japanese patent application Serial No. 11-042752, filed Feb. 22, 1999, having Japanese Publication No. 2000-237328; Japanese patent application Serial No. 11-042753, filed Feb. 22, 1999, having Japanese Publication No. 2000-237329; Japanese patent application Serial No. 11-099008, filed Apr. 6, 1999, having Japanese Publication No. 2000-

288098; Japanese patent application Serial No. 11-099009, filed Apr. 6, 1999, having Japanese Publication No. 2000-288097; PCT patent application WO 2002JP4696, filed May 15, 2002, having PCT Publication No WO03037425; U.S. patent publication No. 2005-0070840 A1, published Mar. 31, 2005; Japanese patent application 2004/317317, filed Oct. 29, 2004; U.S. provisional patent application Ser. No. 60/627,952, filed Nov. 16, 2004; Japanese patent application Ser. No. 2004-347814, filed Nov. 30, 2004; Japanese patent application Ser. No. 2004-357313, filed Dec. 9, 2004; Japanese patent application Ser. No. 2005-027748, filed Feb. 3, 2005; and Japanese patent application Ser. No. 2005-081220, filed Mar. 22, 2005.

Aspects of the embodiments can be modified, if necessary, to employ systems, circuits, and concepts of the various patents, applications, and publications to provide yet further embodiments.

These and other changes can be made to the embodiments in light of the above-detailed description. In general, in the following claims, the terms used should not be construed to limit the invention to the specific embodiments disclosed in the specification and the claims, but should be construed to include all possible embodiments along with the full scope of equivalents to which such claims are entitled. Accordingly, the scope of the invention shall only be construed and defined by the scope of the appended claims.

What is claimed is:

1. A method for screening candidate drugs for iontophoretic delivery, comprising:
    applying an alternating current to a bulk solution comprising at least one drug candidate;
    measuring an impedance response of the bulk solution comprising the at least one drug candidate; and
    ranking the at least one drug candidate for suitability for iontophoretic delivery based in part on the measured impedance response of the bulk solution comprising the at least one drug candidate.

2. The method according to claim 1 wherein measuring the impedance response of the bulk solution comprising the at least one drug candidate comprises measuring the impedance response at two or more frequencies of the alternating current.

3. The method according to claim 1 wherein measuring the impedance response of the bulk solution comprising the at least one drug candidate comprises obtaining at least one of an amplitude or a phase shift of a response signal at two or more frequencies of the alternating current.

4. The method according to claim 1, further comprising:
    determining a flux value based in part on the measured impedance response of the bulk solution comprising the at least one drug candidate.

5. The method according to claim 1 wherein the bulk solution comprises two or more candidate drugs.

6. The method according to claim 1, further comprising:
    measuring the impedance response of a composition comprising at least one drug candidate through at least one resistive element; and
    ranking the composition comprising the at least one drug candidate based in part on the measured impedance response through the at least one resistive element.

7. An assay for determining the iontophoretic deliverability of a pharmaceutical composition, comprising:
    applying an alternating current to a bulk solution comprising the pharmaceutical composition;
    measuring at least one impedance response of the pharmaceutical composition with an impedance spectrometer;
    correlating the at least one measured impedance response to an iontophoretic transport value estimate for the pharmaceutical composition; and
    ranking the pharmaceutical composition for iontophoretic deliverability based in part on the iontophoretic transport value estimate.

8. The assay according to claim 7 wherein the pharmaceutical composition comprises at least one candidate drug compound.

9. The assay according to claim 7 wherein measuring the impedance response of the pharmaceutical composition comprises measuring the impedance response at two or more frequencies of the alternating current.

10. The assay according to claim 7 wherein measuring an impedance response of the pharmaceutical composition comprises: obtaining at least one of a magnitude or a phase shift of a response signal for the pharmaceutical composition, with an impedance spectrometer, at two or more frequencies of the alternating current.

11. A method for screening candidate drugs for iontophoretic delivery, comprising:
    applying an alternating current to a composition comprising at least one drug candidate a bulk solution;
    measuring through at least one resistive element an impedance response of the composition comprising the at least one drug candidate in the bulk solution; and
    ranking the composition comprising the at least one drug candidate based in part on the measured impedance response of the composition comprising the at least one drug candidate in the bulk solution.

12. The method according to claim 11 wherein measuring the impedance response of the composition comprising the at least one drug candidate in the bulk solution comprises measuring the impedance response at two or more frequencies of the alternating current.

13. The method according to claim 11 wherein measuring the impedance response of the composition comprising the at least one drug candidate in the bulk solution comprises obtaining at least one of an amplitude or a phase shift of a response signal at two or more frequencies of the alternating current.

14. The method according to claim 11, further comprising:
    determining a flux value based in part on the measured impedance response of the composition comprising the at least one drug candidate in the bulk solution.

15. The method according to claim 11 wherein the composition comprises two or more candidate drugs in the bulk solution.

* * * * *

UNITED STATES PATENT AND TRADEMARK OFFICE
CERTIFICATE OF CORRECTION

| | | |
|---|---|---|
| PATENT NO. | : 7,998,745 B2 | Page 1 of 1 |
| APPLICATION NO. | : 11/850597 | |
| DATED | : August 16, 2011 | |
| INVENTOR(S) | : Gregory A. Smith | |

It is certified that error appears in the above-identified patent and that said Letters Patent is hereby corrected as shown below:

Title Pg, Item 56:
"2006/0024358 A1 2/2006 Santini et al. 424/448" should read, --2006/0024358 A1 2/2006 Santini, JR. et al. 424/448--.

Column 12, Line 31:
"at least one drug candidate a bulk solution;" should read, --at least one drug candidate in a bulk solution;--.

Signed and Sealed this
Sixth Day of December, 2011

David J. Kappos
*Director of the United States Patent and Trademark Office*